United States Patent
Dobyns, III

(10) Patent No.: US 6,722,577 B2
(45) Date of Patent: Apr. 20, 2004

(54) CONTAINER FOR DISPENSING AROMATIC LIQUID

(76) Inventor: Simon L. Dobyns, III, 318 U St. NW., Washington, DC (US) 20001

( * ) Notice: Subject to any disclaimer, the term of this patent is extended or adjusted under 35 U.S.C. 154(b) by 44 days.

(21) Appl. No.: 09/948,593

(22) Filed: Sep. 10, 2001

(65) Prior Publication Data

US 2003/0047618 A1 Mar. 13, 2003

(51) Int. Cl.[7] .............................. A24F 25/00; A61L 9/04
(52) U.S. Cl. .............................. 239/34; 239/37; 239/38; 239/39; 239/40
(58) Field of Search .............................. 239/34, 37, 39, 239/38, 40, 41, 42, 43, 44, 46, 49, 51, 57

(56) References Cited

U.S. PATENT DOCUMENTS

| | | | | |
|---|---|---|---|---|
| 1,211,306 A | * | 1/1917 | Freese | 239/42 |
| 3,727,840 A | * | 4/1973 | Nigro | 239/43 |
| 4,247,042 A | * | 1/1981 | Schimanski et al. | 239/43 |
| 4,293,095 A | * | 10/1981 | Hamilton et al. | 239/35 |
| 4,995,555 A | * | 2/1991 | Woodruff | 239/43 |
| 5,749,519 A | * | 5/1998 | Miller | 239/44 |

* cited by examiner

*Primary Examiner*—Davis D Hwu

(57) ABSTRACT

Aromatic liquids substances such as deodorizers, room freshener compositions, perfumes, fragrances and the like are dispensed in vapor phase from a container holding the substance in liquid phase. In the best mode, the container is in conical form, having a controlled opening or openings through which the liquid volatile substance is dripped downwardly onto a conical substrate, from which it is dispensed in vapor phase into the atmosphere. The dispenser is configured such that it may stand, as on a counter or any flat surface, or may be hung, as in a closet, in an automobile, or the like.

10 Claims, 5 Drawing Sheets

CONTAINER FOR DISPENSING AROMATIC LIQUID

BACKGROUND OF THE INVENTION

The present invention relates to apparatus for packaging and distributing an aromatic liquid, to be dispensed in the aromatic phase. Particularly, this invention relates to apparatus for dispensing deodorizers, air fresheners, perfumes, aromatizing agents, fragrances, and the like into the surrounding air, but may be used to dispense other aromatic agents into the atmosphere.

A number of various vapor releasing air treatment devices have been described in the literature and manufactured. In some devices, the aromatic vaporizable substance is incorporated into a solid carrier medium from which the substance evaporates and enters the atmosphere, frequently, after a protective wrapping or cover is opened or removed. In other prior devices, the aromatic vaporizing substance is packaged in liquid form, and discharged in some manner into the atmosphere, in vapor form. The current invention relates to the latter type of apparatus.

More particularly, the instant invention relates to a gravity fed liquid system air treatment device, in which the rate of dispersion of the aromatic volatile substance is substantially even over a period of time, and which rate of dispersion may be adjusted according to the desire of the user.

In one known type of gravity fed dispensing system, the aromatic liquid is held in an inverted bottle supported within a cup or pan holding a pool of liquid at the bottom thereof. The mouth of the bottle is positioned a short distance above the bottom of the cup or pan, facilitating the flow of liquid from the bottle, until the liquid level reaches the mouth of the bottle, and the flow is stopped by atmospheric pressure. As soon as sufficient liquid evaporates, such that the level of liquid in the pan falls below the mouth of the bottle, flow from the bottle begins again, and the liquid level is maintained at the level of the mouth of the bottle. Should this device be disturbed and knocked over, or should the parts of the dispensing device be displaced in any way, the contents of the cup or pan is spilled, and the liquid flow from the bottle continues. The results of the disturbance and spillage include waste of the evaporating liquid, spillage requiring clean-up, and excessive release of aromatic vapors, which may be unpleasant, or even noxious. Such devices are described in: Gubelman U.S. Pat. No. 436,130; Peek U.S. Pat. No. 1,099,730; Dupuy U.S. Pat. No. 2,481,296 and Rooch U.S. Pat. No. 2,586,179.

In another known type of gravity fed system, various provisions are made for preventing the evaporation of the volatile aromatic liquid until such is desired by the user. Provisions include the use of a screw threaded bottle and removable cap, or a closure having screw threads, such as in U.S. Pat. Nos. 1,755,901; 1,818,648; 1,974,414; 2,166,969 and 2,586,179. Such dispensers having screw-treaded necks or closures are cumbersome to manufacture and use.

In other inverted bottle evaporators, the user must make a puncture of the closed end to provide an opening through which the volatile liquid may seep. If the opening is too small or too large, an undesirable rate of evaporation will take place, resulting in insufficient dispensing of the aromatic liquid with ineffective results of the deodorizer liquid or the like, or excessive dispensing of the liquid, resulting in excessive vapors, which are unpleasant, or possible noxious.

A number of attempts have been made to devise methods or apparatus which regulate the dispensing and diffusion rates of volatile materials, especially with regard to fragrant substances, and their uses in enclosed rooms. The primary function of these devices in commercial use has been for the deodorizing and elimination or masking of malodors. Additionally, however, the controlled release of fine fragrances for aesthetic or utilitarian appeal, and use, adds to the need for a device which is simple to manufacture and use, and which is able to control the dispensing rate of the aromatic volatile liquid.

The present invention discloses a device which is an advance over what is known in this area. The present invention provides a dispenser characterized by the simplicity and versatility thereof.

SUMMARY OF THE INVENTION

It is therefore an object of the present invention to provide a simplified and improved gravity fed package and dispenser for the dispensing of volatile aromatic vapor into the air.

It is an additional object of the present invention to provide a gravity fed air treatment dispenser that is spill-proof.

It is an additional object of the present invention to provide an improved air treatment dispenser that enables the volatile aromatic liquid to be dispensed in vapor form in a predetermined, uniform manner.

It is a still further object of the present invention to provide such an improved air treatment dispenser in which the emitted fragrance level is adjustable.

With regard to all of the foregoing objects of the present invention, it is an aim of the present invention to provide a new and improved air treatment, volatile aromatic liquid dispensing device that is significantly effective while being simple in construction, economical to manufacture, and which is easy to use.

BRIEF DESCRIPTION OF THE DRAWINGS

Reference is made to the accompanying drawings in which are shown illustrative embodiments of the invention, from which its novel features and advantages will be apparent.

DESCRIPTION OF THE PREFERRED EMBODIMENT

Figure 1:
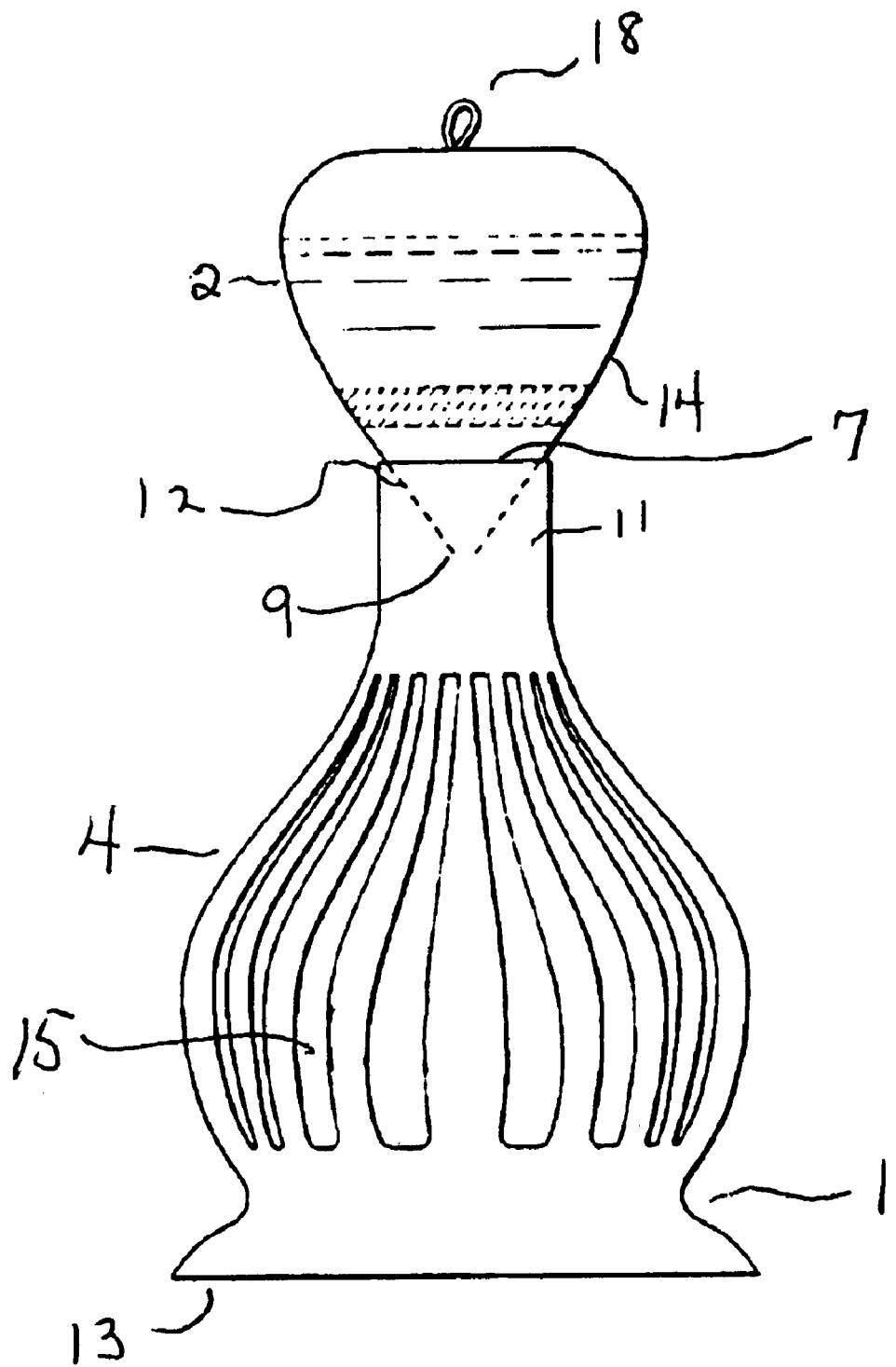
FIG. 1 is a side elevational view showing the container with its optional hanging attachment.

Referring to FIG. 1, it will be seen that the container 1 includes a top section 2 and a bottom section 4. The container is generally hourglass shaped, having preferably a flat bottom 13, such that the container can rest upon a flat surface.

The top section 2 includes a see-through generally ovoid-shaped portion 14, which initially holds the aromatic liquid to be dispensed into the air. The liquid-containing portion 14 is securably held by neck member 11, which joins bottom section 4. Neck member 11 is roughly tubular shaped, securing the top and bottom portions 2, 4 to one another so that no leakage or overflow of the aromatic liquid can occur.

The top section further includes a slightly conical section 12, so that the aromatic liquid will collect efficiently at the bottom end of the conical section, to be dispensed through aperture 9. The top section also includes a closure or filter mechanism 7, which may be adjusted to control the relative flow of aromatic liquid toward the dispensing aperture 9.

The top section optionally may include a hook or loop like device 18, so that the device may be hung my means of a cord, string, hook, or other device as desired.

The bottom section 4 may be formed of plastic in a molding operation with neck portion 11 as an integral unit. The bottom surface 13 of the bottom section is preferably formed with raised sides at 8, so that unwarranted excess aromatic liquid, which had been released into the bottom section, will not overflow onto exterior surfaces. The bottom and neck sections optionally may be formed separately, and secured together with appropriate adhesive means. Bottom section 4 is molded with multiple apertures 15, which permit the evaporation of the volatile liquid into the ambient atmosphere.

As shown, the apertures 15 of bottom section 4 are elongated, roughly rectangular shapes. The shapes of the apertures may be formed in any decorative shape or pattern, to facilitate the dispensing of aroma into the surrounding atmosphere. It is preferred that the apertures are of a size, such that a child would be unable to insert his hand into the interior of the device, and of such a size to prevent household pets from entering the device.

Figure 2:
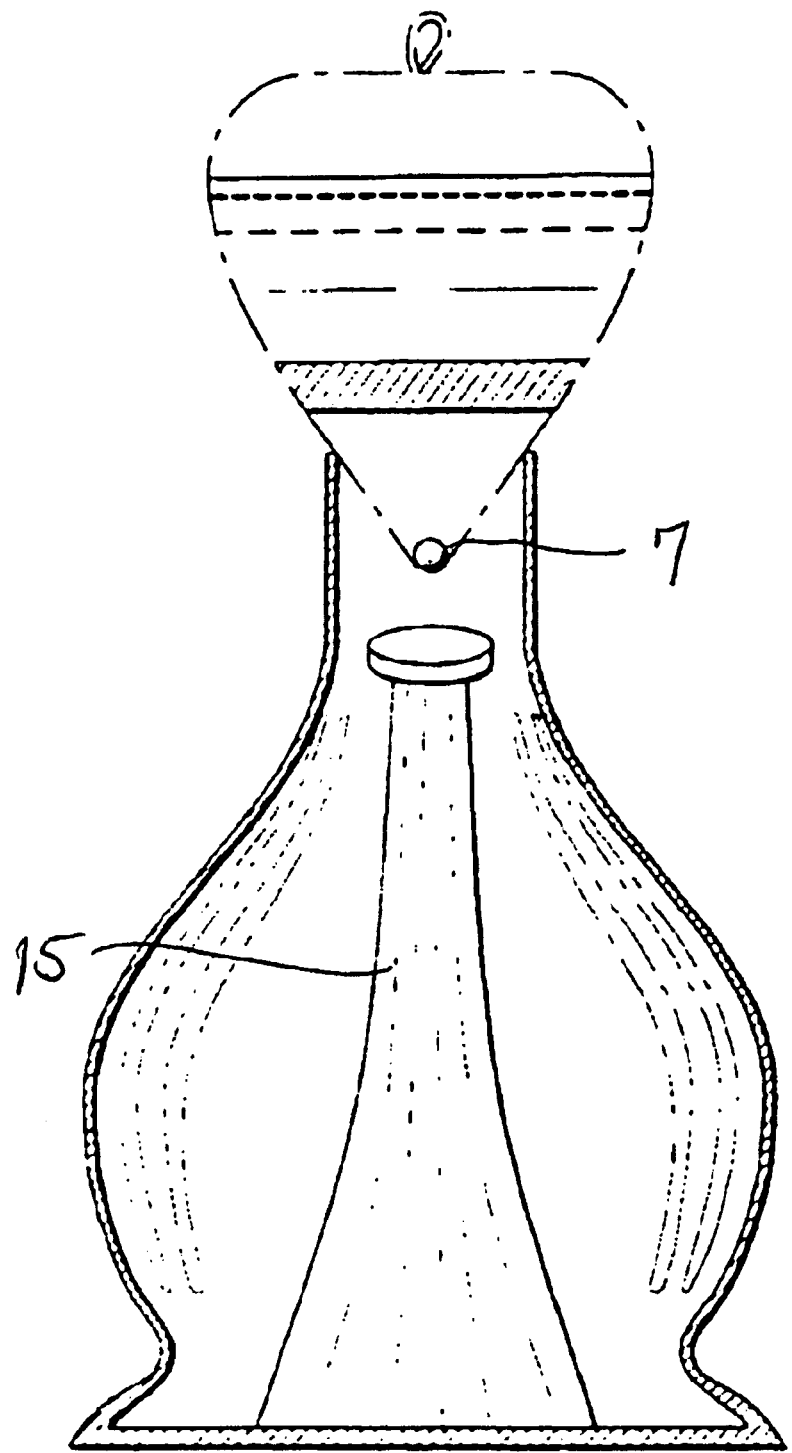
FIG. 2 is an enlarged sectional view of a portion of the container.

The top section 2 is formed separately from bottom section 4, and includes a valve section 7, as shown in FIG. 2. The valve may be of any means known in the art, but is preferably actuated by a simple twist, or rotation of the outer valve surface.

Neck member 11 connects top section 2 to bottom section 4, either as molded together in a integral unit, or securably fastened by suitable adhesive. In addition, neck portion provides additional means to prevent accidental spillage of the volatile aromatic liquid contained in top section 2. Should valve mechanism at 7 fail, the gravity-fed liquid from top section 2 would be retained in neck section 11, until it could be suitably absorbed by absorbent member 15.

Figure 3:
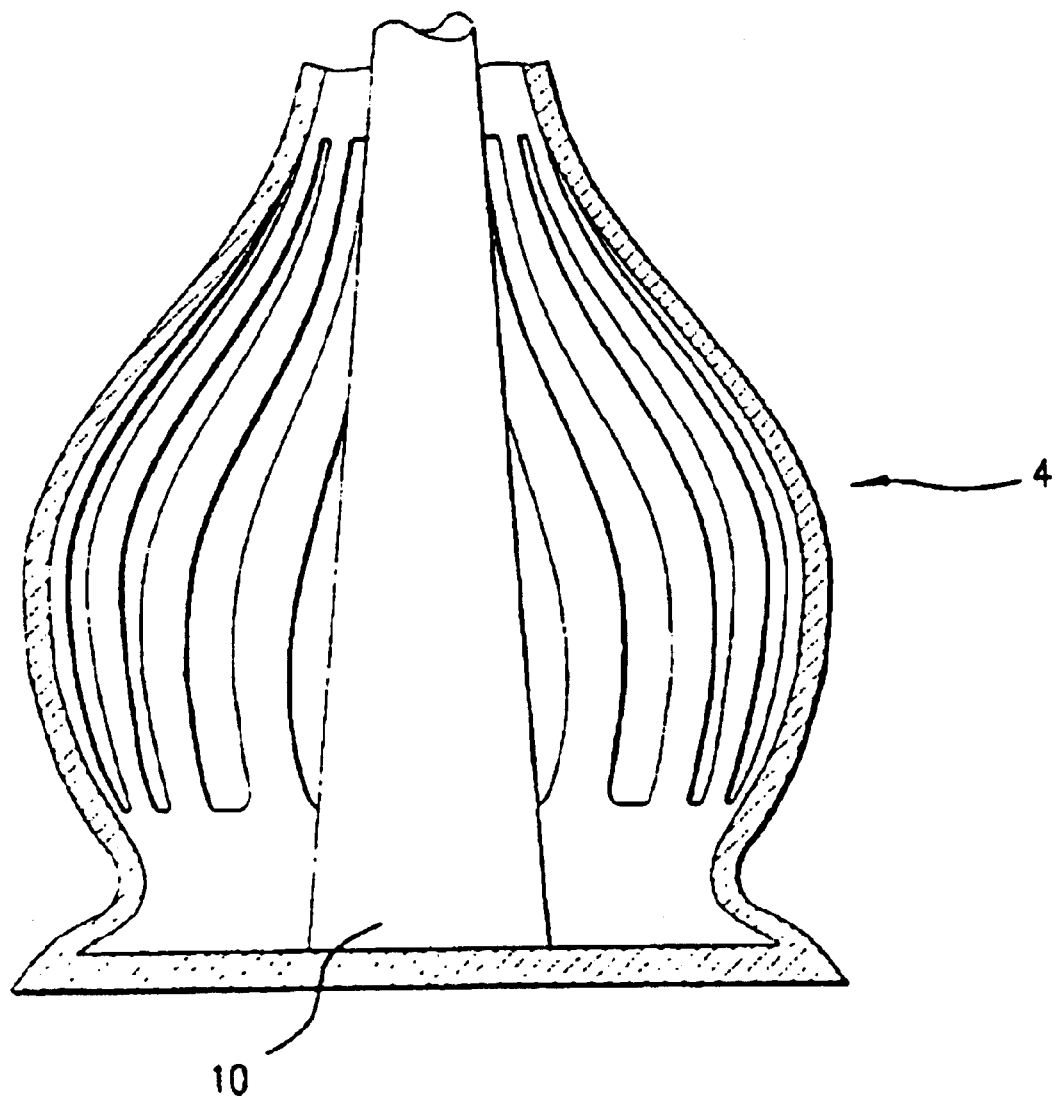
FIG. 3 is a side exploded view of a portion of the container.
Figure 4:
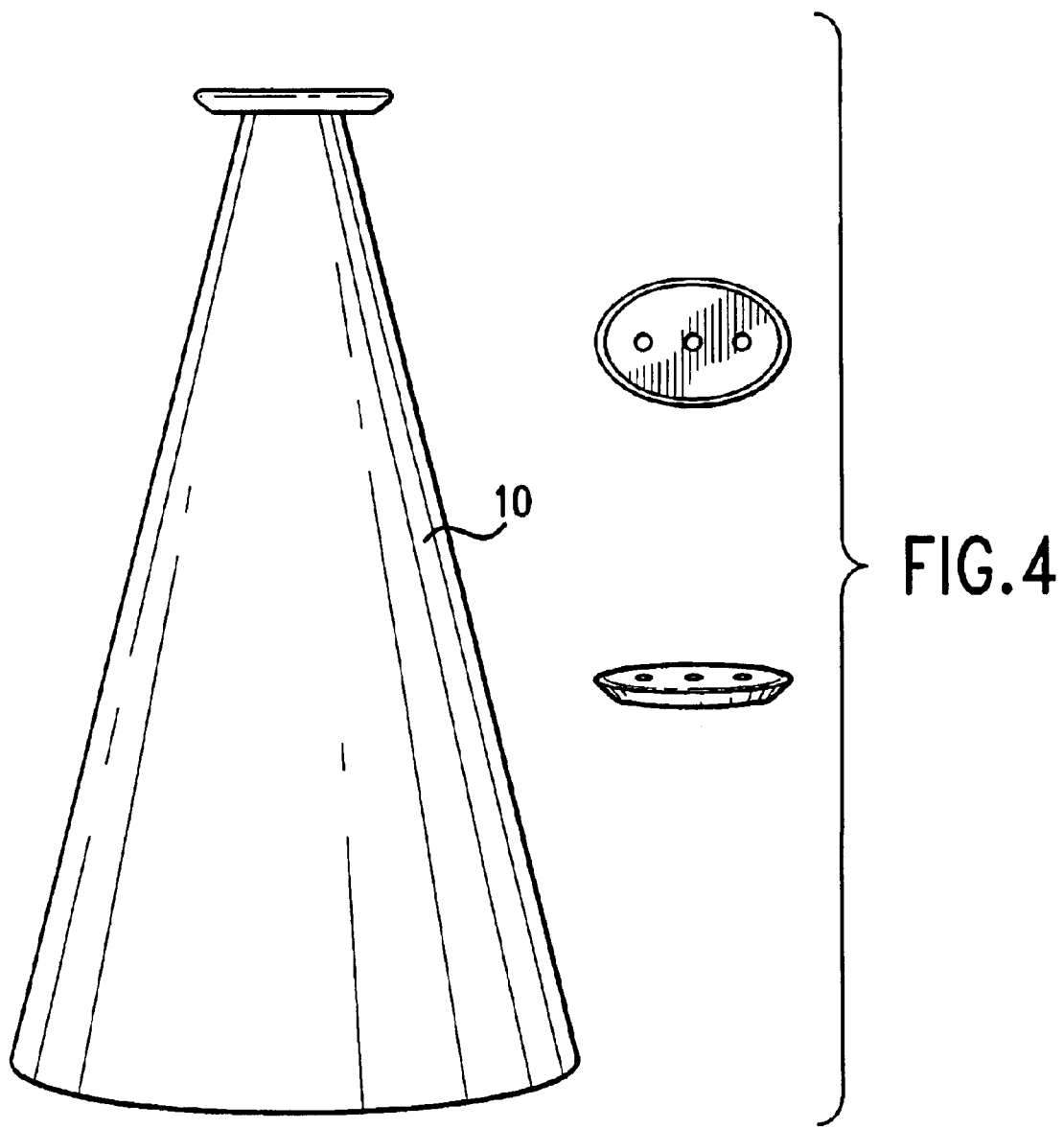
FIG. 4 is a side elevational view showing the internal dispensing means for the aromatic liquid.

FIG. 3 is an exploded view of bottom section 4, which shows the bottom structure opened to show the evaporating unit 10. Evaporating unit 10 is formed of a fibrous material which may be, illustratively, cloth, paper, or polymer fibers. The material is absorbent of the aromatic liquid, and then released the liquid by evaporation into the air. The evaporating unit may be formed in any shape, but is preferably conical shaped, to provide increased exposed surface area for evaporation of the volatile liquid.

In operation, the valve 7 is opened, permitting the aromatic liquid to flow downwardly into the conical end 12 of the top section. The liquid then drips through the aperture 9, onto fibrous evaporating unit 10, where it is released into the air.

Figure 5:
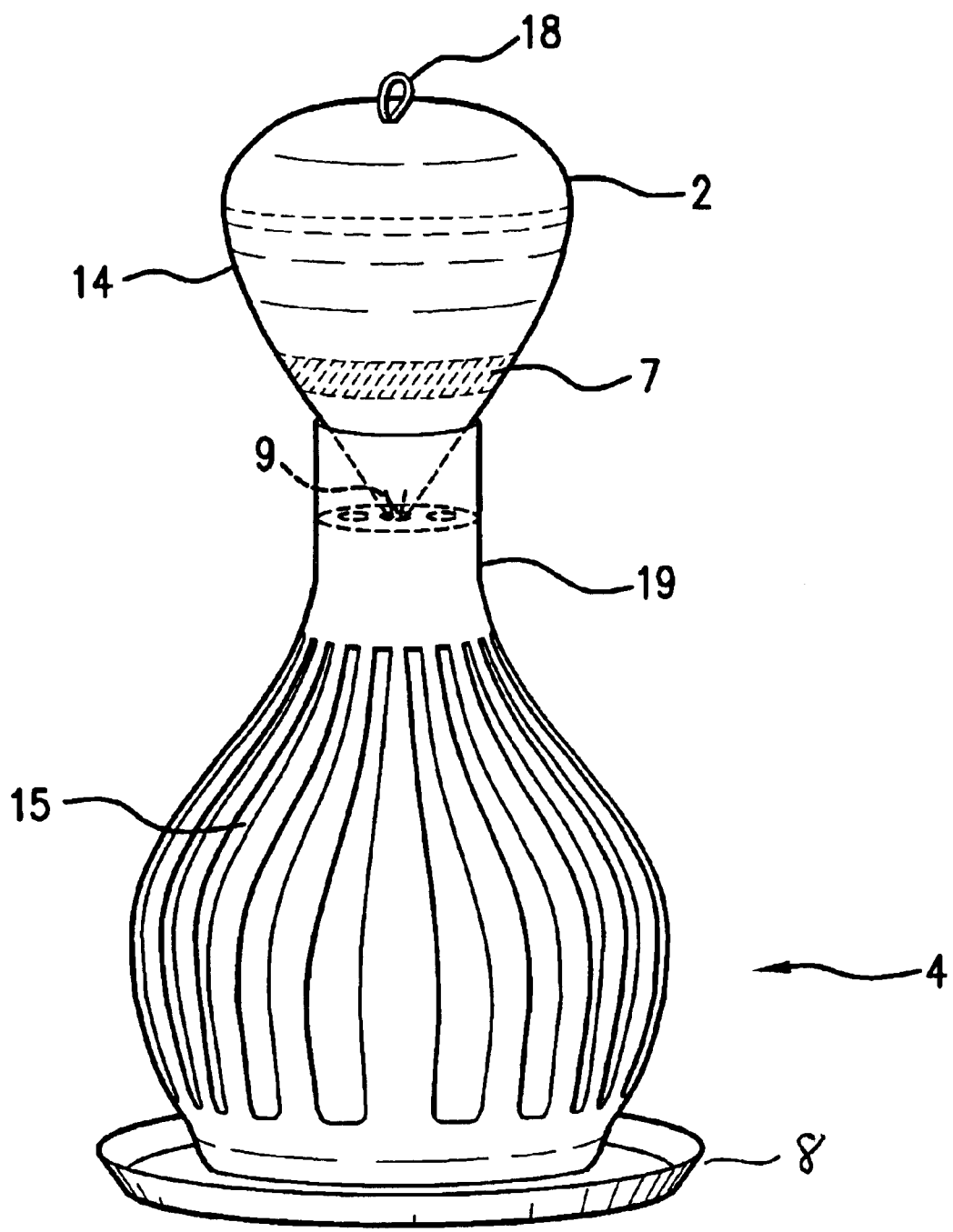
FIG. 5 is a side elevational view showing an alternate embodiment of the invention.

FIG. 5 illustrates an alternate embodiment of the device. While it is anticipated that the principal use of the invention is for the dispensing of volatile aromatic substances into the atmosphere for aesthetic purposes, FIG. 5 illustrates an embodiment for another purpose. In FIG. 5, top section of the device contains an aromatic liquid which is attractive to flying insects. In bottom section 4, of FIG. 5, the fibrous evaporating unit 17 would be treated with an adhesive substance, such that as flying insects were attracted by the aromatic evaporating liquid to the surface of evaporating unit 10, the insects would adhere to the surface.

In this embodiment of the invention, bottom section apertures 15 would be of size and shape sufficient to provide adequate ingress for the flying insects, but of a pattern that would disguise the trapped insects, and provide an aesthetically pleasing appearance.

What I claim is:

1. A vapor releasing air treatment device comprising:
   a container having at least one opening therein,
   a supply of volatile aromatic liquid,
   a valve member at the container opening,
   a back-up valve means for the retention of excess liquid
   a conical shaped absorbent surface for the receipt and retention of the received aromatic liquid;
   an apertured housing for the containment of the conical shaped absorbent surface on which is retained the received aromatic liquid;
   wherein said volatile aromatic liquid is held within the container, and then may pass by means of the valve member, through the back-up valve means, onto the conical shaped absorbent surface.

2. The vapor releasing device according to claim 1, wherein the apertured housing has a thickened saucer-like bottom portion, to prevent spilling of said volatile aromatic liquid.

3. The vapor releasing device according to claim 2, wherein the absorbent receiving surface is treated with an insect-adhering substance.

4. The vapor releasing device according to claim 1, wherein the absorbent aromatic liquid receiving surface is conical shaped.

5. The vapor releasing device according to claim 1, wherein the container is formed of transparent material.

6. The vapor releasing device according to claim 1, wherein the container portion is joined to the absorbent receiving surface housing are adhesively joined.

7. The vapor releasing device according to claim 1, wherein the container portion is adhesively joined to the absorbent receiving surface housing.

8. The vapor releasing device according to claim 1, wherein the volatile aromatic liquid is an air freshener.

9. The vapor releasing device according to claim 1, wherein the volatile aromatic liquid is an insect attractant.

10. The vapor releasing device according to claim 1, wherein the back-up valve means for the retention of excess liquid may be formed of transparent material.

* * * * *